(12) United States Patent
Holt et al.

(10) Patent No.: US 6,436,697 B1
(45) Date of Patent: Aug. 20, 2002

(54) ENZYME-MEDIATED SYNTHESIS OF PEPTIDOMIMETICS

(75) Inventors: Karen Holt; Stephen John Clifford Taylor, both of Cambridge; Peter David Tiffin, Herts, all of (GB)

(73) Assignee: Darwin Discovery, Ltd. (GB)

( * ) Notice: Subject to any disclaimer, the term of this patent is extended or adjusted under 35 U.S.C. 154(b) by 0 days.

(21) Appl. No.: 09/425,484

(22) Filed: Oct. 22, 1999

(30) Foreign Application Priority Data

Oct. 23, 1998 (GB) .............................................. 9823334

(51) Int. Cl.[7] .......................... C12P 13/02; C12P 41/00
(52) U.S. Cl. ........................ 435/280; 435/128; 435/129
(58) Field of Search ................................ 435/280, 128, 435/129

(56) References Cited

U.S. PATENT DOCUMENTS

| 3,897,480 A | 7/1975 | Mita et al. |
| 5,728,876 A | 3/1998 | Balkenhohl et al. |

FOREIGN PATENT DOCUMENTS

| WO | 9202617 | 2/1992 |
| WO | 9635714 | 11/1996 |
| WO | 9703783 | 2/1997 |

OTHER PUBLICATIONS

Wang, Yi–Fong et al. (1997) "Cross–Linked Crystals of Subtilisin: Versatile Catalyst for Organic Synthesis" *J. Org. Chem.* 62(11):3488–3495.

Moree, Wilna J. et al. (1997) "Exploitation of Subtilisin BPN' as Catalyst for the Synthesis of Peptides Containing Noncoded Amino Acids, Peptide Mimetics and Peptide Conjugates" *J. Am. Chem. Soc.* 119(17):3942–3947.

Persichetti, Rose A. et al. (1995) "Cross–Linked Enzyme Crystals (CLECs) of Thermolysin in the Synthesis of Peptides" *J. Am. Chem. Soc.* 117:2732–2737.

Zelinski, Thomas, Herbert Waldmann (1997) "Cross–Linked Enzyme Crystals (CLECs): Efficient and Stable Biocatalysts for Preparative Organic Chemistry" *Angew. Chem. Int. Ed. Engl.* 36(7):722–724.

*Primary Examiner*—Sandra E. Saucier
(74) *Attorney, Agent, or Firm*—Saliwanchik, Lloyd & Saliwanchik

(57) ABSTRACT

A process for the preparation of a compound of formula (1)

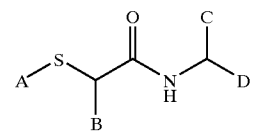

(1)

comprises reacting compounds of formulae (2) and (3)

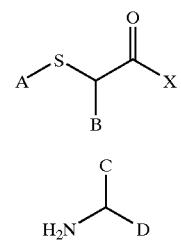

(2)

(3)

in the presence of an enzyme, wherein A is a thiol-protecting group, B, C and D are each the same or different organic groups of up to 30 C atoms, optionally functionalized at any position, provided that neither a primary amine nor a primary amide is present, and X is a group that can be displaced by $NH_2$.

18 Claims, No Drawings

ENZYME-MEDIATED SYNTHESIS OF PEPTIDOMIMETICS

FIELD OF THE INVENTION

This invention relates to the synthesis of peptidomimetics via enzyme-mediated coupling.

BACKGROUND OF THE INVENTION

Peptidomimetics, and particularly α-thiopeptidomimetics, have been shown to inhibit many enzymes, including matrix metalloproteinases, which are implicated in a broad range of inflammatory diseases such as rheumatoid and osteoarthritis, also bone degradation in osteoporosis and congestive heart failure, e.g. as described in WO 96/11209, WO 96/35714 and WO 97/03783. This family of enzymes is also implicated in at least three aspects of cancer, metastasis, invasive growth and angiogenesis. Peptidomimetics constructed from single enantiomer constituents may offer the greatest potential to effect selective inhibition of matrix metalloproteinases and thereby achieve useful therapeutic benefit.

Peptidomimetic compounds can be accessed by conventional formation of amide linkages using standard coupling reagents such as 1-(3-dimethylaminopropyl)-3-ethylcarbodiimide hydrochloride (J. C. Sheehan et al., *J. Org. Chem.*, 1961, 26, 2525–2528) or mixed anhydrides, but such methods with these coupling reagents are expensive, and activated intermediates may be susceptible to racemisation, resulting in a diastereomeric mixture of products. An alternative methodology is to use an enzyme, which avoids racemisation; furthermore, if one of the components in the reaction is racemic or in an optically enriched, but not optically pure, state, then the stereospecificity of the enzyme can be exploited to effect both coupling and resolution of that component in a single step. If such an enzyme possesses good stability, and is available in immobilised form, then enzymic peptide bond formation becomes economically attractive since the enzyme can be recovered and reused.

WO 92/02617 discloses that enzymes can be crystallised and cross-linked in situ, e.g. with glutaraldehyde, to give highly insoluble derivatives. Such enzymes, known as CLECs, are high performance regio- and stereoselective catalysts, some of which are suitable for peptide bond formation. They possess increased stability relative to the native enzyme, especially at elevated temperatures and in the presence of high concentrations of polar organic solvents, conditions under which the native enzymes are not active. Organic solvent mixtures are useful for enzymic peptide synthesis, since they can be designed to allow maximum solubility of substrates but have low solubility for the product, which may precipitate during the biotransformation driving the reaction to completion.

The synthesis of a number of peptides containing both natural and unnatural α-amino acids has been described using both enzymes and more specifically CLEC's such as PeptiCLEC-TR. See Zelinski and Waldmann, Angew. Chem. Int. Ed. Engl. 36:722–4 (1997), Persichetti et al, J. Am. Chem. Soc. 117:2732–7 (1995).

U.S. Pat. No. 5,728,876 discloses the resolution of amines by enzyme-catalysed acylation.

Yi-Fong et al, J. Org. Chem. 62(11):3488–95 (1997), discloses cross-linked crystals of subtilisin as a versatile catalyst for organic synthesis.

Moree et al, JACS 119(17):3942–7 (1997), discloses subtilisin BPN as a catalyst for the synthesis of certain peptides.

U.S. Pat. No. 3,897,480 discloses, as intermediates in the preparation of N-(mercaptoacetyl) aminoacids, benzoyl-protected forms thereof.

SUMMARY OF THE INVENTION

This invention is based on the surprising discovery that enzyme-catalysed coupling of compounds of formulae (2) and (3) provides compounds of formula (1) with high efficiency.

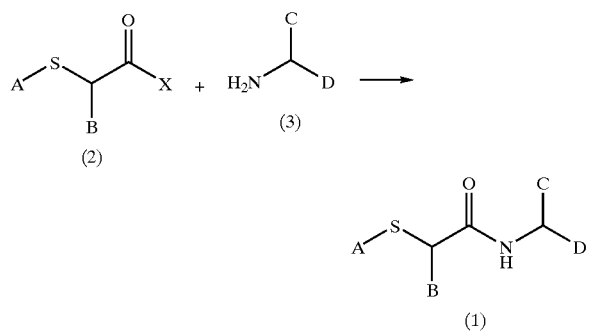

According to the invention, a process for obtaining peptide-like compounds, or precursors to such compounds, comprises the biotransformation of an optically pure or racemic α-substituted carboxylic acid derivative of formula (2) with an optically pure or racemic amino acid derivative (3), or an analogue, having a free amine group. Such reaction forms the amide bond and a new peptidomimetic product. It is noteworthy that, if the α position in (2) is either unsubstituted, or for example is substituted with bromine, no coupling is observed.

In a preferred embodiment of the present invention, the enzyme in this process is thermolysin, and whilst the free enzyme can be used in solution to effect a single coupling reaction, the cross-linked enzyme crystalline form shows much greater stability allowing its recovery and reuse. Simple separation of the product (1) is also facilitated.

A significant advantage of this method is that both or one of the substrates may be optically pure, racemic, or optically active. In the case where a racemic component is utilised in the coupling, the unreacted isomer may subsequently be racemised and reutilised in the coupling reaction.

In the given formulae, A is a thiol-protecting group, B, C and D are each the same or different organic groups of up to 30 C atoms, optionally functionalised at any position, provided that neither a primary amine nor a primary amide functionality is present, and X is a group that can be displaced by $NH_2$. It is particularly preferred that A is aroyl, e.g. benzoyl, owing to the stability of the protecting group during the biotransformation; certain compounds of formulae (1) and (2), wherein A is aroyl, are novel and represent a further aspect of this invention.

DESCRIPTION OF THE INVENTION

Compounds of formula (2) have a free functional group X, e.g. where COX comprises a carboxyl group, and is substituted at the α position with sulfur. This thiol group in the α position is preferentially protected. Suitable protecting groups are acyl and aroyl groups of up to 20 C atoms. Specific examples are acetyl, benzoyl or benzyloxycarbonyl. Additionally the side-chain may be protected as either a homo or hetero-disulfide, where the former example is the most atom-efficient protecting group. Enzyme-catalysed couplings of this nature with a free thiol group at this, or adjacent positions, generally are very inefficient due to the inactivation of the enzyme. The group B, at the α position, can be variable, and is limited only by the intrinsic enzyme specificity.

Compounds of formula (3) have a free amine group. They may also have a carboxyl at the α position which is protected, for example as a methylamide or in the form of a dipeptide where the second amino acid terminates with a protected carboxyl group, for example as the methylamide. The functionality C, α to the free amine, can vary and can be either structurally similar to or the same as the natural specificity for the enzyme.

Various enzymes may be used. Examples include thermolysin (in which case X is preferably OH) or subtilisin (in which case X may be $OR^1$, $R^1$ being any esterifying group such as a hydrocarbon group of up to 30 C atoms, e.g. $C_{1-6}$ alkyl). The enzyme is preferably provided as a CLEC.

As indicated above, the nature of each of B, C and D is not especially limited, except perhaps by enzyme specificity. This will be understood by, and can be handled by appropriate measures known to, one skilled in the art. Each may be, for example, aliphatic such as alkyl or aryl such as phenyl or naphthyl, optionally substituted by one or more functional or non-functional groups.

In a typical biotransformation, the acid and amine substrates (2) and (3) are dissolved in a solvent mixture, such as 40% ethanol in water containing 10 mM calcium acetate, and then the enzyme is added to start the reaction. The heterogeneous mixture is stirred at 40–50° C., and as the product is formed it precipitates. Alternatively, a biphasic system of ethyl acetate and either water or 10 mM calcium acetate in water can be used. Surprisingly, it has been found that high substrate concentrations, of >100 g/l, were well tolerated. Upon completion of the reaction, as judged by HPLC, the enzyme can then be recovered by filtration, and found to retain much of its activity for use in subsequent cycles.

This reaction may leave a crude product solution. If the substrates are optically pure, then the product may be precipitated and recovered by filtration, after distillation of solvents to concentrate the solution. If resolution and coupling have been performed at the same time, then aqueous acid (such as hydrochloric acid) or aqueous base (such as sodium bicarbonate) washing can be used first to remove the unwanted ionic substrate. The products from resolution-coupling reactions may be both enantiomerically and diastereomerically enriched, typically in >95% ee and >95% de. The thiol-protecting group can be removed, if necessary or desired, by methods known to those skilled in the art.

The process according to the invention has several advantages over conventional peptide-like synthesis. Recycling the enzyme allows greater economy, and optically pure substrates are not required. Furthermore, the products are stereoisomerically pure, and the reactions proceed at volume efficiencies greater than would be expected for conventional enzymic peptide synthesis. In addition, unconverted acid substrate (2), enriched in the unreactive enantiomer, can be racemised by reaction with a suitable basic or acidic reagent, preferably in the presence of an essentially anhydrous organic solvent. More preferably, a non-nucleophilic organic base such as DABCO is used to effect racemisation.

The following Examples illustrate the invention.

EXAMPLE 1

(S)-2-Benzoylsulfanyl-5-(1,3-dioxo-1,3-dihydroisoindol-2-yl)pentanoic acid (62.6 g, 0.163 mol) and (S)-2-amino-4-methylpentanoic acid (2,2-dimethyl-1-(S)-methylcarbamoylpropyl)amide (40 g, 0.155 mol) were dissolved in a biphasic mixture of ethyl acetate (480 mL) and water (240 mL) at 45° C. and stirred to equilibrate for 10 min. An HPLC reference sample was removed for t=0. The PeptiCLEC-TR enzyme (40 mL) is added to the reaction and the reaction is stirred at 45° C. Samples are removed at regular intervals for HPLC analysis which shows that the reaction is complete in 2 hours. Filtration of tile enzyme followed by acidic then basic aqueous washes gives a solution of (S)-2-[(S)-2-benzoylsulfanyl-5-(1,3-dioxo-1,3-dihydroisoindol-2-yl)pentanylamino]-4-methylpentanoic acid (2,2-dimethyl-1(S)-methylcarbamoylpropyl)amide which is then evaporated to dryness to give the product as a glass foam 80 g, 83%.

EXAMPLE 2

Ethyl acetate and water are charged to a jacketed vessel and heated to approximately 45° C. (S)-2-Amino-4-methylpentanoic acid (2,2-dimethyl-1-(S)-methylcarbamoylpropyl)amide is then added. The PeptiCLEC-TR is charged followed by racemic 2-benzoylsulfanyl-4-(3,4,4-trimethyl-2,5-dioxoimidazolin-1-yl)butyric acid (2.05 eq) and the temperature maintained at 43–47° C. The reaction is monitored by HPLC and upon completion the mixture is filtered to remove the PeptiCLEC-TR, washing through with water and ethyl acetate. The organic phase is washed sequentially with sodium hydrogen carbonate solution and then water, to remove unreacted starting materials enriched in (R)-2-benzoylsulfanyl-4-(3,4, 4-trimethyl-2,5-dioxoimidazolin-1-yl)butyric acid. The organic phase is then washed with 2M HCl, to remove residues of the starting dipeptide, and deionised water. The organic phase is then concentrated/azeodried by distillation. The product generally crystallises spontaneously, and the suspension is cooled and aged before isolation by filtration. The (S)-2-[(S)-2-benzoylsulfanyl-4-(3,4,4 -trimethyl-2,5-dioxoimidazolidin-1-yl)butyrylamino]-4-methylpentanoic acid (2,2-dimethyl-1(S)-methylcarbamoylpropyl)amide is dried in a vacuum oven at 50° C. to constant weight.

In order to improve utilisation of the reactants, the (R)-enriched α-benzoylsulphanyl acid starting material is recycled by extraction and racemisation.

To the aqueous sodium bicarbonate solution of starting materials is added isopropyl acetate (4 vol). The pH is adjusted to 1–2 using hydrochloric acid, 36%. The resulting mixture is filtered, washing through with isopropyl acetate (0.5 vol). The layers are separated, and the upper organic layer is washed with deionised water. The resulting solution is heated to reflux under Dean Stark conditions until no further water is collected. Isopropyl acetate (2 vol) is distilled. At this stage the percentage water should be ≦0.1%. The batch is cooled and isopropyl acetate (1.5 vol) is charged.

DABCO (0.1 equiv.) is charged. The batch is heated to reflux (90° C.). The racemisation is monitored by HPLC. The reaction typically takes between four and five hours.

The reaction mixture is cooled, and washed with 1M hydrochloric acid solution (2 vol), then with water (2 vol). The resulting organic solution is distilled at atmospheric pressure, until 2.5 vol have been collected. Toluene (4 vol) is charged, and distillation continued, until a further 4 vol of solvent is collected. Then toluene (2 vol) is charged. The final volume should be approximately 5 volumes relative to acid starting material. The batch is cooled to 75–80° C., and seeded with acid. The batch is allowed to cool slowly to room temperature and stirred overnight. The batch is then cooled in ice for ≦1 h. The batch is filtered, and washed with toluene (1 vol), then dried under vacuum to constant weight at 80–75° C.

What is claimed is:

1. A process for the preparation of a compound of formula (1)

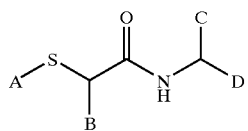

which comprises reacting compounds of formulae (2) and (3)

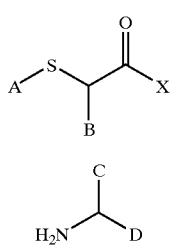

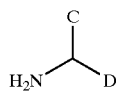

in the presence of an enzyme that can catalyze the reaction of the compounds of formulae (2) and (3) to form the compound of formula (1), wherein A is an acyl or aroyl group of up to 10 C atoms, and wherein B, C and D are each the same or different organic groups of up to 30 C atoms, optionally functionalised at any position, provided that neither a primary amine nor a primary amide is present, and X is a group that can be displaced by $NH_2$, wherein the enzyme is selected from the group consisting of thermolysin and subtilisin.

2. The process according to claim 1, wherein A is benzoyl.

3. The process according to claim 1, wherein the enzyme is in the form of a cross-linked enzyme crystal.

4. The process according to claim 1, wherein D is CON$(R)_2$, wherein each R is independently H or an organic group, but the R's are not both H.

5. The process according to claim 1, wherein D incorporates one or more α-amino acid residues of (S) configuration at the α centre.

6. The process according to claim 1, wherein X is $OR^1$ and $R^1$ is H or an esterifying function of up to 30 C atoms.

7. The process according to claim 6, wherein $R^1$ is H.

8. The process according to claim 1, wherein the enzyme is stereoselective.

9. The process according to claim 8, wherein the compound of formula (3) is a single stereoisomer.

10. The process according to claim 8, wherein the compound of formula (3) is a mixture of stereoisomers.

11. The process according to claim 8, wherein the compound of formula (2) is in the form of a predominantly single enantiomer, of 90% ee or higher.

12. The process according to claim 8, wherein the compound of formula (2) is in racemic form or is a non-racemic mixture of enantiomers of less than 90% ee.

13. The process according to claim 1, which additionally comprises removing the thiol-protecting group.

14. The process according to claim 9, wherein the compound of formula (2) is used in the form of a predominantly single enantiomer, of 90% ee or higher.

15. The process according to claim 9, wherein the compound of formula (2) is in racemic form or is a non-racemic mixture of enantiomers of less than 90% ee.

16. The process according to claim 10, wherein the compound of formula (2) is in the form of a predominantly single enantiomer, of 90% ee or higher.

17. The process according to claim 10, wherein the compound of formula (2) is in racemic form or is a non-racemic mixture of enantiomers of less than 90% ee.

18. The process according to claim 12, which additionally comprises racemising unreacted compound of formula (2).

* * * * *